(12) United States Patent
Sokabe et al.

(10) Patent No.: US 9,290,735 B2
(45) Date of Patent: Mar. 22, 2016

(54) MAMMARY GLAND EPITHELIAL CELL CULTURE

(75) Inventors: Masahiro Sokabe, Nagoya (JP); Kishio Furuya, Nagoya (JP); Go Tazaki, Tsukuba (JP); Hitoshi Tsuruta, Tsukuba (JP); Motohiro Fukuda, Tsukuba (JP)

(73) Assignees: National University Corporation Nagoya University, Nagoya-shi (JP); KURARAY Co., Ltd., Kurashiki-shi (JP)

( * ) Notice: Subject to any disclaimer, the term of this patent is extended or adjusted under 35 U.S.C. 154(b) by 959 days.

(21) Appl. No.: 12/866,588

(22) PCT Filed: Feb. 5, 2009

(86) PCT No.: PCT/JP2009/051991
§ 371 (c)(1),
(2), (4) Date: Aug. 6, 2010

(87) PCT Pub. No.: WO2009/099153
PCT Pub. Date: Aug. 13, 2009

(65) Prior Publication Data
US 2010/0331216 A1   Dec. 30, 2010

(30) Foreign Application Priority Data
Feb. 6, 2008 (JP) ................................. 2008-026385

(51) Int. Cl.
*C12N 5/071* (2010.01)
*C12N 5/00* (2006.01)
*C12M 1/32* (2006.01)
*C12M 3/06* (2006.01)
*C12M 1/00* (2006.01)

(52) U.S. Cl.
CPC ............. *C12N 5/0631* (2013.01); *C12M 23/12* (2013.01); *C12M 23/16* (2013.01); *C12M 23/22* (2013.01); *C12N 5/0062* (2013.01); *C12N 2535/10* (2013.01)

(58) Field of Classification Search
CPC .. C12N 15/85; C12N 2503/04; C12N 5/0631; C12N 5/0697; C12N 2502/095; C12N 2830/85; C12N 5/0018; C12N 5/0062
See application file for complete search history.

(56) References Cited

U.S. PATENT DOCUMENTS 6,287,790 B1 * 9/2001 Lelievre et al. .............. 435/7.23
2009/0017540 A1   1/2009 Nishio et al.

FOREIGN PATENT DOCUMENTS

JP   2006-191809   7/2006

OTHER PUBLICATIONS

U.S. Appl. No. 13/229,087, filed Sep. 9, 2011, Tazaki, et al.

* cited by examiner

*Primary Examiner* — Blaine Lankford
(74) *Attorney, Agent, or Firm* — Oblon, McClelland, Maier & Neustadt, L.L.P.

(57) ABSTRACT

To provide a cell culture method capable of sustaining in-vivo functions for a long time by suppressing dedifferentiation. A cell culture method in accordance with the present invention is to culture cells in a multi-layered state in a minute partitioned space and to obtain a tissue structure having a function resembling an in-vivo function. When the cells are mammary gland epithelial cells, a hollow acinus-like structure can be formed. The minute partitioned space is particularly preferably a micro container in a cell culture container having a plurality of such micro containers on the surface.

5 Claims, 4 Drawing Sheets

MAMMARY GLAND EPITHELIAL CELL CULTURE

TECHNICAL FIELD

The present invention relates to a cell culture method.

BACKGROUND ART

A technique of using cells isolated from tissue for tests and examinations is essential in biotechnology-related fields. Such a technique is widely used for a diagnosis of diseases and pathoses, a search for a new drug and an assessment of its effect, an animal inspection, a plant inspection, a test of an environment pollutant and so on. Therefore, cells used in the biotechnology field are becoming increasingly diversified.

Although some isolated cells are immediately used for tests in a floating state, others are cultured in a state of being adherent to a culture dish and used for various tests and examinations in most cases. Primary cells and cell lines used for cell culture are required to exhibit drug sensitivity, toxicity reaction or the like of a similar level to a test in vivo, so-called an in vivo test. In other words, an in vivo-like cell function is required in a cell culture container. Further, because isolation for obtaining primary cells is complicated and cell culture lines used for a cell culture test are expensive, a test method with a small number of cells is desired.

In the above-described cell culture test, its effect is measured under the same conditions while changing the amount, concentration, and the like of the drug or the like to be evaluated. Therefore, the cell culture containers need to be identical in material, shape, and the like. As for the cell culture container, a plastic petri dish, a glass petri dish, a glass plate fixed in a container, a well plate, and the like are usually used. Examples of the well plate include plates and petri dishes each including 6 wells, 12 wells, 48 wells, or 96 wells. In general, these plates have substantially the same overall size. Therefore, as the number of wells increases, the size of a single well becomes smaller. A single well corresponds to a single culture dish. With the recent trend toward miniaturization, a 384-well plate including a number of culture dishes with a small diameter has also come to be used. The bottom of each of these culture dishes has a flat plate shape, and this bottom surface is used as a culture surface.

However, when a conventional cell culture container is used to culture tissue cells, these cells sometimes lose their original functions, thus causing dedifferentiation. This causes a problem that the intended cell function is not developed.

To solve the above-described problem, an attempt to coat the surface of a culture container with biological material (such as glycoprotein and protein) derived from a human or an animal (see Patent document 1) as well as an attempt to culture such material in a polymer gel (see Patent document 2) have been made.
[Patent Document 1]
Japanese Unexamined Patent Application Publication No. 8-317786
[Patent Document 2]
International Patent Publication No. WO03/006635

DISCLOSURE OF INVENTION

Technical Problem

However, there are problems in the method disclosed in Patent document 1 including a problem that since the biological material to be coated is specially prepared, it is expensive.

In addition, it is very difficult to form a uniform cell aggregation by suppressing the dedifferentiation. The method disclosed in Patent document 2 has also problems including a problem that the size of the cell aggregation cannot be controlled and a problem that a microscopic observation cannot be easily performed. For example, in the case of mammary gland epithelial cells of a mouse, there is a problem that even when cells are cultured on a culture dish coated with collagen, the cells are cultured into a paving-stone shape and becomes a dedifferentiated state. Further, in the case where they are cultured in a collagen gel, there is a problem that they are not formed into an acinus structure resembling an in-vivo structure. In addition, a microscopic observation is very difficult.

An object of the present invention is to provide a cell culture method capable of sustaining in-vivo functions for a long time by suppressing dedifferentiation.

Technical Solution

A cell culture method in accordance with the present invention is to culture cells in a multi-layered state in a minute partitioned space and to obtain a tissue structure having a function resembling an in-vivo function. Note that the "multi-layered" means that cells are stacked one another into two or more layers. The cells are preferably primary cells. Further, the cells are particularly preferably mammary gland epithelial cells, because, if so, a hollow acinus-like structure can be formed.

Further, the minute partitioned space is particularly preferably a micro container in a cell culture container having a plurality of such micro containers on the surface. Note that the area of the base of the micro container is preferably $9 \times 10^{-4}$ mm$^2$ to $9 \times 10^{-2}$ mm$^2$; the height of the sidewall is preferably 15 μm to 300 μm; and the width of the sidewall is preferably 3 μm to 15 μm. Further, adjacent micro containers are preferably communicated with each other by an opening, and the width of the opening is preferably 3 μm to 20 μm. Furthermore, in order to make a microscopic observation easier, the region of the cell culture container in which the micro containers are formed preferably has transparency.

Advantageous Effects

In accordance with the present invention, a cell culture method capable of sustaining an in-vivo function for a long time by suppressing dedifferentiation can be provided.

EXPLANATION OF REFERENCE

Figure 1A:
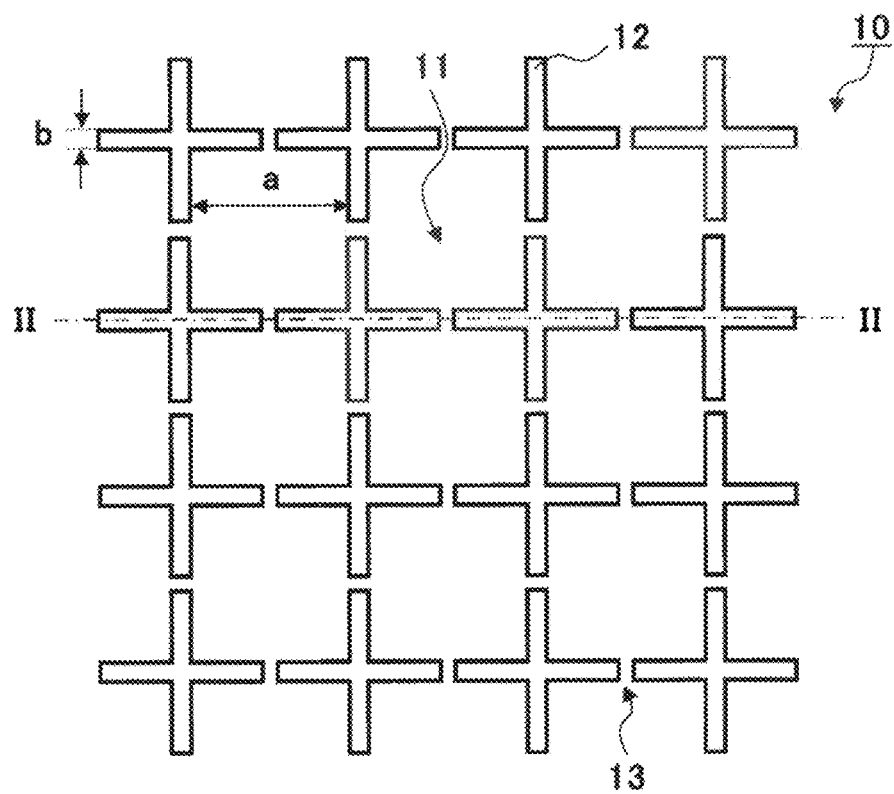
FIG. 1A is a plane view showing a structure of a cell culture container in accordance with a first exemplary embodiment.

10 CELL CULTURE CONTAINER
11 MICRO CONTAINER
12 SIDEWALL
13 OPENING

BEST MODE FOR CARRYING OUT THE INVENTION

The present invention maintains a differentiated state by forming cells into multiple layers within a micro container, and thereby developing a function resembling an in-vivo function. Mammary gland epithelial cells are dedifferentiated on a commercially-available dish. We have found out that mammary gland epithelial cells maintain their differentiated state in a micro container, form an acinus structure resembling the in-vivo structure, and produces butterfat droplets.

On the surface of a culture container used in a culture method in accordance with the present invention, a concave-convex pattern, i.e., a plurality of micro containers, i.e., culture spaces are formed. By optimizing the width and height of sidewalls (convex portions) that partition the culture container into the micro containers, cells are cultured only within the micro containers and a uniform differentiated state can be maintained. Note that it is also conceivable to form partitioned culture spaces made of gel instead of using the micro containers.

It is necessary to adjust the size of the micro container surrounded by the sidewalls to the optimal range for culturing cells. Too large bottom surface of the micro container partially makes cells longer and thinner and prevents the formation of the uniform multi-layered state as in the case of culturing on a flat plate. On the other hand, too small bottom surface of the micro container makes the containment of cells impossible. Therefore, the size of the space is preferably adjusted to such a range that several to several tens of cells can be contained according to the type of cells to be cultured.

Further, the sidewalls of the micro container also need to be adjusted to the optimal range for culturing cells. Too wide width of the sidewalls makes cells stick on the top surface of the sidewalls, thus making the micro containers inappropriate for the culturing. Too narrow width of the sidewalls makes the manufacturing very difficult. Too low height of the sidewalls lets cells climb over the sidewalls, thus making the micro containers inappropriate for the culturing. Too high height of the sidewalls makes the manufacturing very difficult. In addition, it also makes substances less prone to be diffused, thus deteriorating the culturing environment.

Further, by adopting the structure in which an opening is provided in each sidewall so that a plurality of adjacent micro containers are communicated with each other, it is possible to supply oxygen and nutrition to the cells and supply physiological active material produced by the cells with efficiency. Further, with the openings, cell aggregations, which are formed into multiple layers, have a contact point with each other, thus enabling the differentiated state to be maintained. Note that by adjusting the area of the base of the micro containers, the height of the sidewalls, and/or the width of the openings as appropriate according to the type of cells to be cultured, the culture container can be applied to various culture systems.

Exemplary embodiments of the present invention are explained hereinafter. However, the present invention is not limited to the exemplary embodiments shown below. Further, for clarifying the explanation, the following description and the drawings are simplified as appropriate.

Exemplary Embodiments

Figure 1B:
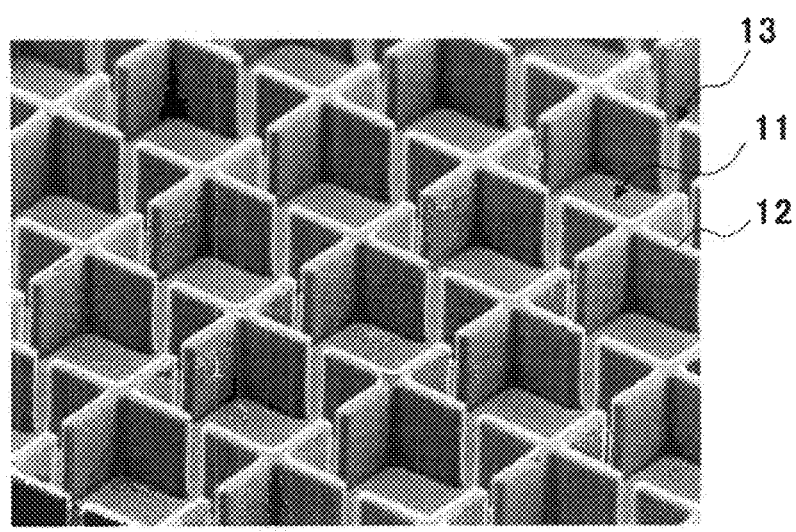
FIG. 1B is a SEM perspective image showing a structure of a cell culture container in accordance with Example 1.
Figure 2:
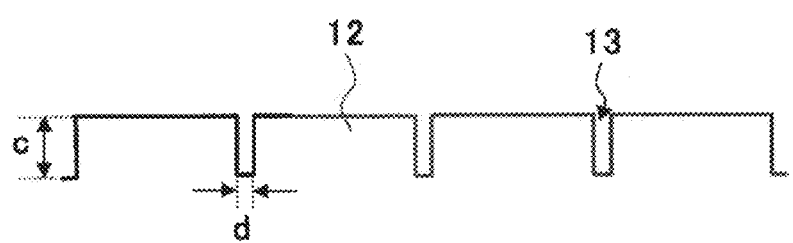
FIG. 2 is a cross-section showing a structure of a cell culture container in accordance with Example 1.

A structure of a cell culture container used in a cell culture method in accordance with an exemplary embodiment is explained with reference to FIGS. 1A, 1B and 2. FIG. 1A is a plane view showing a structure of a cell culture container in accordance with this exemplary embodiment, and FIG. 1B is a SEM perspective image of the same. Further, FIG. 2 is a cross-section taken along the line II-II of FIG. 1A. As shown in FIGS. 1A, 1B and 2, a cell culture container 10 includes macro containers 11, sidewalls 12, and openings 13. The plurality of sidewalls 12 are formed in a mesh shape on the culture surface of the cell culture container 10, and spaces surrounded by the sidewalls 12 serves as the macro containers 11. Further, each of the openings 13 is formed at a central portion of each side of the sidewalls 12 which are formed on the four sides of each of the macro containers 11.

In FIGS. 1A, 1B and 2, a width "a" of the base of each of the macro containers 11, a width "b" and a height "c" of each of the sidewalls 12 for partitioning the cell culture container into the macro containers 11, and a width "d" of each of the openings 13 for allowing adjacent macro containers 11 to communicate with each other are shown.

The shape of the bottom surface of the macro containers 11 is not limited to any particular shape. That is, a square, a circle, and a polygon as well as other various shapes can be adopted. The area of the bottom surface is preferably $9 \times 10^{-4}$ mm$^2$ to $9 \times 10^{-2}$ mm$^2$. Further, an isotropic shape is preferably used. When the bottom surface is rectangular, the long side of the bottom surface is preferably 1 to 1.5 times the short side.

The width "b" of each of the sidewalls 12 is preferably such a width that no cell sticks on the upper surface of the sidewalls 12 so that cells are formed into multiple layers and cultured only in the macro containers 11. For example, when mammary gland epithelial cells of a mouse are cultured, it is preferably 3 μm to 15 μm.

When mammary gland epithelial cells of a mouse is cultured, for example, the height "c" of each of the sidewalls 12 is preferably 15 μm to 300 μm so that the cells are formed into multiple layers and cultured in the macro containers 11.

The width "d" of each of the openings 13 for allowing adjacent macro containers 11 to communicate with each other is preferably such a width that cultured cells are prevented from moving from a micro container 11 in which the cultured cells are originally seeded to an adjacent micro container 11 and that only one cell can come into contact with a cell seeded in the adjacent micro container 11. Alternatively, it may be such a width that only one cell or two can move to an adjacent micro container 11. For example, when the diameter of a cultured cell is 20 μm, it is preferably 3 μm to 20 μm.

Figure 3:
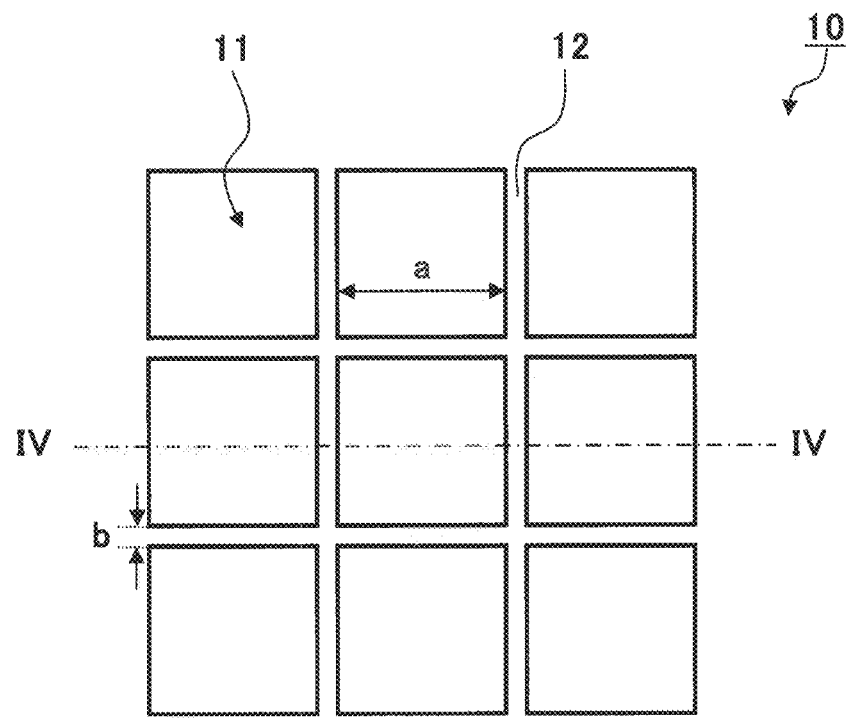
FIG. 3 is a plane view showing a structure of a cell culture container.
Figure 4:
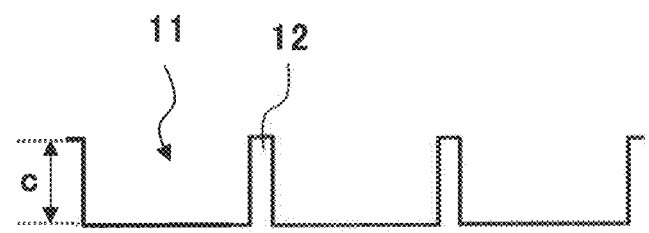
FIG. 4 is a cross-section showing a structure of a cell culture container.

Note that as shown in FIGS. 3 and 4, the macro containers 11 may be completely surrounded by the sidewalls 12 on the four sides. Note also that FIG. 3 is a plane view showing a structure of another type of macro containers in accordance with this exemplary embodiment and FIG. 4 is a cross-section taken along the line IV-IV of FIG. 3.

The method of manufacturing a concave-convex pattern on a cell culture container used in a cell culture method in accordance with the present invention is not limited to any particular method. Examples of the method include transfer molding using a mold, three-dimensional optical modeling, precision machining, wet etching, dry etching, laser processing, and electrical discharge machining. The actual manufacturing method may be preferably selected from these manufacturing methods in view of the intended use, required processing accuracy, costs, and the like of the cell culture container.

As a specific example of the transfer molding method using a mold, a method for forming a concave-convex pattern by resin molding using a metal structure as a mold may be employed. This method is preferred because it can reproduce the shape of the metal structure on a resin as a concave-convex pattern with a high transcription rate, and because the raw material cost can be reduced by using a general-purpose resin material. Such a method using a mold of a metal structure is superior in terms of low costs and because it can satisfy high dimensional accuracy.

Examples of the above-described metal structure manufacturing method include plating treatment, precision machining, wet etching, dry etching, laser processing, and electrical discharge machining on a resist pattern produced by photolithography or a resin pattern produced by three-dimensional optical modeling. The actual method may be selected as appropriate in view of the intended use, required processing accuracy, costs, and the like.

Examples of the method of forming a concave-convex pattern on a resin using the metal structure obtained in the above-described manner as a mold include injection molding, press molding, monomer casting, solvent casting, hot embossing, and roll transfer by extrusion molding. However, the injection molding is preferably used in view of its productivity and transcription property.

The material used to form the cell culture container of the present invention is not limited any particular material, provided that the material has a self-supporting property. Examples of the material include synthetic resin, silicon, or glass. However, a transparent synthetic resin is preferably used as the material in view of costs and cell visibility under microscopic observation. Examples of the transparent synthetic resin include acrylic resins such as polymethyl methacrylate and methyl methacrylate-styrene copolymer, styrene resin such as polystyrene, olefin resin such as cycloolefin, ester resins such as polyethylene terephthalate and polylactic acid, silicone resin such as polydimethylsiloxane, and polycarbonate resin. These resins may contain various additives such as colorant, dispersing agent, and thickening agent, unless the transparency is impaired.

In the cell culture container used in a cell culture method in accordance with the present invention, surface treatment may be performed on the front-surface side of the concave-convex pattern and a modified layer and/or a coating layer may be formed for the purpose of improving the hydrophilic properties, biocompatibility, cellular affinity, and the like of the container surface.

The above-described method for forming a modified layer is not limited to any particular method, provided that a method with which the self-supporting properties are impaired and a method causing extreme surface roughness of 100 μm or more are not employed. Examples of the method include chemical treatment, solvent treatment, chemical treatment such as introduction of a graft polymer by surface graft polymerization, physical treatment such as corona discharge, ozone treatment, and plasma treatment.

In addition, the method for forming the coating layer is not limited to any particular method. Examples of the method include dry coating such as sputtering and vapor deposition, and wet coating such as inorganic material coating and polymer coating.

In order to inject a culture solution without mixing air bubbles therein, it is desirable to impart a hydrophilic property to the surface of the concave-convex pattern. As the method for forming a uniform hydrophilic membrane, inorganic vapor deposition is preferably employed.

When the cellular affinity is taken into consideration, it is more preferable to coat cytophilic proteins such as collagen and fibronectin, for example. In order to uniformly coat a collagen aqueous solution or the like, it is preferable to perform the coating after the above-mentioned hydrophilic membrane is formed. In cell culture, in general, it is desirable to culture cells on an extracellular matrix surface by replicating the in vivo environment. Accordingly, it is particularly preferable to dispose an organic film made of extracellular matrix suitable for cultured cells after an inorganic hydrophilic membrane is uniformly formed as described above.

The cells cultured in a cell culture method in accordance with the present invention are not limited to any particular cells. However, preferable cells are cells that are dedifferentiated in a flat plate. Further, the type of animal may be selected from a rat, a mouse, a chicken, a dog, a monkey, a human, and the like according to the purpose. Examples of the cells include a chondrocyte, an osteoblast, an odontoblast, an ameloblast, a mammary gland epithelial cell, a ciliated epithelial cell, an intestinal epithelial cell, a fat cell, a hepatocyte, a mesangial cell, a glomerulus epithelial cell, a sinusoidal endothelial cell, and a myoblast.

In a cell culture method in accordance with the present invention, it is necessary to seed an appropriate number of cells so that the cells are disposed only within micro containers used for culturing cells and formed into multiple layers within those spaces. Therefore, the density with which cells are seeded is preferably $1.0 \times 10^4$ to $1.0 \times 10^6$ cells/cm$^2$. For example, when the micro container has a square shape and each side of the square is 100 μm, it is preferably $5.0 \times 10^4$ to $5.0 \times 10^5$ cells/cm$^2$. Under such conditions, it is possible to culture cells in a multi-layered state and to obtain differentiated cells.

EXAMPLE

Next, examples of a cell culture container in accordance with the present invention are explained. However, the present invention is not limited to examples shown below.
<Preparation of Mammary Gland Epithelial Cells>
After anesthetizing a mouse in the later stages of pregnancy or in a lactation period with ether, mammary gland tissue was extracted by dislocating the cervical vertebrae. The extracted tissue was cut into small pieces by using a blade replacement type scalpel, treated with Dispase (II, GODO SHUSEI Co., Ltd., 2000 PU/ml) at 37° C. for 90 minutes and with Collagenase (type III, Wothington, 0.5 mg/ml) at 37° C. for 8 minutes, filtered by a nylon filter, and dispersed in a culture solution in order to obtain mammary gland epithelial cells.
<Culture Method>
DME/F12 (Sigma) added with 1-2% Serum Replacement 2 (Sigma) was used as the culture solution. Further, EGF (epithelial growth factor) 50 ng/ml and insulin 5 μg/ml were added to the culture solution. The cells were cultured with 5% $CO^2$ at 37° C. for three days to three weeks, during which a half of the culture solution was replaced with a new culture solution once every two or three days.

Example 1

A concave-convex pattern shape shown in FIGS. 1A, 1B and 2 in which a=100 μm, b=10 μm, c=50 μm, and d=10 μm was manufactured by a photolithography, and then Ni electroplating was performed to obtain a mold having a corresponding concave-convex shape. By using the mold, pattern transcription was performed on polymethyl methacrylate by hot embossing to manufacture a resin base material with the above-mentioned size. A silicon dioxide film was formed to 100 nm thickness on the surface of the resin base material by vacuum deposition, and then γ-ray sterilization was performed to obtain a concave-convex pattern base material. After the concave-convex base material was coated with I-type collagen, mammary gland epithelial cells of a mouse were cultured.

Comparative Example 1

The same resin base material of polymethyl methacrylate having a flat plate shape as that used in Examples 1 and 2 was manufactured. A silicon dioxide film was formed to 100 nm thickness on the surface of the resin base material by vacuum deposition, and then γ-ray sterilization was performed to obtain a concave-convex pattern base material. After the concave-convex base material was coated with 1-type collagen, mammary gland epithelial cells of a mouse were cultured.

Figure 5:
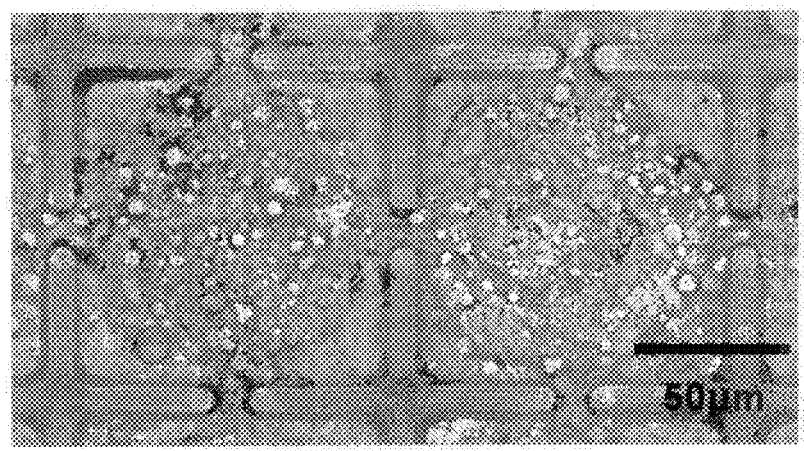
FIG. 5 is an image by an optical microscope of cells cultured by a cell culture method in accordance with Example 1.
Figure 7:
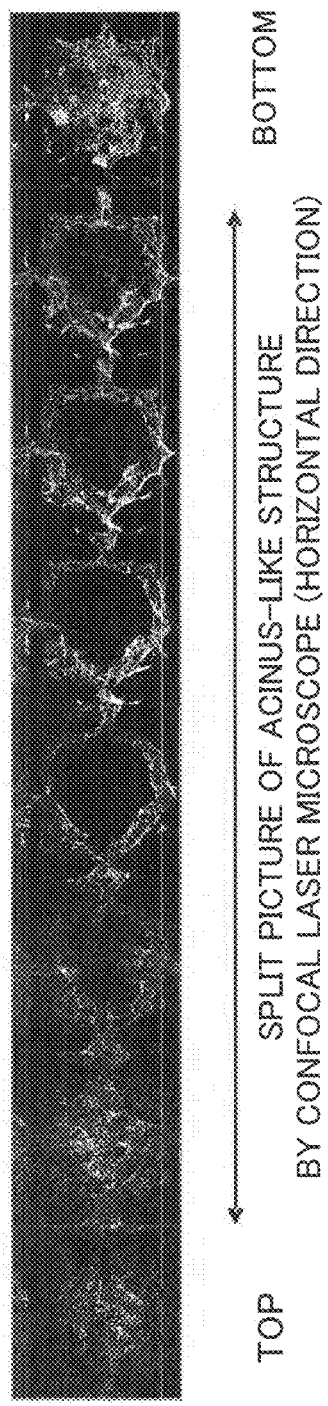
FIG. 7 is an image by a confocal laser microscope of cells cultured by a cell culture method in accordance with Example 1.

As shown in FIG. 5, mammary gland epithelial cells on the eighth day of the culturing in Example 1 were cultured in a multi-layered state. Further, they maintained a differentiated state and produced a butterfat droplet. FIG. 7 shows an image that is obtained as the focus point of a confocal laser microscope is moved vertically downward. As obvious from FIG. 7, a hollow acinus structure was formed.

Figure 6:
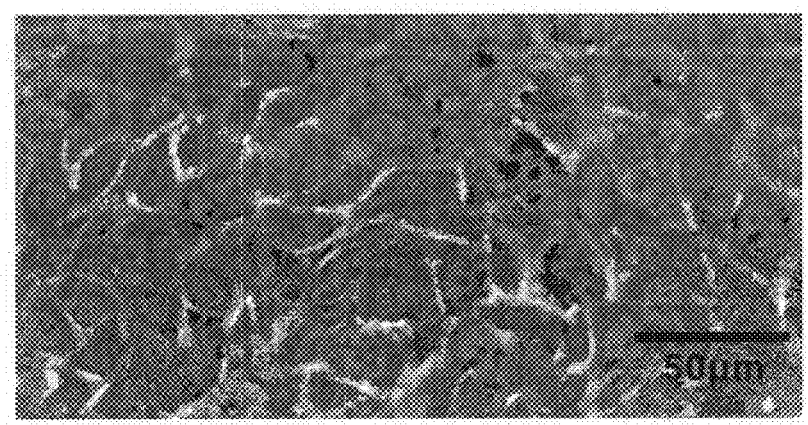
FIG. 6 is an image by an optical microscope of cells in accordance with Comparative Example 1.

By contrast, as shown in FIG. 6, mammary gland epithelial cells on the eighth day of the culturing in Comparative Example 1 maintained the single-layer state and the dedifferentiated state.

INDUSTRIAL APPLICABILITY

The present invention can be applied to cell culture methods of culturing cells isolated from tissue.

The invention claimed is:
1. A cell culture method comprising:
    culturing cells in a multi-layered state in a minute partitioned space and obtaining a tissue structure having a function resembling an in-vivo function,
    wherein the minute partitioned space is a micro container in a cell culture container having a plurality of micro containers on a surface,
    wherein adjacent micro containers are communicated with each other with an opening formed in a sidewall partitioning the adjacent micro containers, and a width of the opening is 3 μm to 20 μm, and
    wherein the cells are mammary gland epithelial cells.
2. The cell culture method according to claim 1, wherein the cells are primary cells.
3. The cell culture method according to claim 1, wherein the mammary gland epithelial cells are differentiated and form a hollow acinus structure.
4. The cell culture method according to claim 1, wherein a base area of the micro container is $9\times10^{-4}$ mm$^2$ to $9\times10^{-2}$ mm$^2$; a height of a sidewall is 15 μm to 300 μm; and a width of a sidewall is 3 μm to 15 μm.
5. The cell culture method according to claim 1, wherein a region of the cell culture container in which a micro container is formed has transparency.

* * * * *